US008764800B2

(12) United States Patent
Johansson et al.

(10) Patent No.: US 8,764,800 B2
(45) Date of Patent: Jul. 1, 2014

(54) DISPLACEMENT DEVICE, USE AND SYSTEM THEREFORE

(75) Inventors: Erik Johansson, Uppsala (SE); Niklas Axen, Järlasa (SE); Sven Olerud, Länna (SE); Staffan Bowald, Fjärdhundra (SE); Hans Jacobsen, Taby (SE)

(73) Assignee: Ortoviva AB (SE)

( * ) Notice: Subject to any disclaimer, the term of this patent is extended or adjusted under 35 U.S.C. 154(b) by 0 days.

(21) Appl. No.: 12/994,654

(22) PCT Filed: May 28, 2009

(86) PCT No.: PCT/SE2009/000275
§ 371 (c)(1),
(2), (4) Date: Apr. 12, 2011

(87) PCT Pub. No.: WO2009/145696
PCT Pub. Date: Dec. 3, 2009

(65) Prior Publication Data
US 2011/0190820 A1 Aug. 4, 2011

Related U.S. Application Data

(60) Provisional application No. 61/130,490, filed on May 30, 2008.

(30) Foreign Application Priority Data

May 28, 2008 (SE) ...................................... 8012460

(51) Int. Cl.
*A61B 17/70* (2006.01)
(52) U.S. Cl.
USPC .......................................................... 606/246
(58) Field of Classification Search
USPC .................... 606/99, 53, 54, 57–59, 246–279; 600/201–244
See application file for complete search history.

(56) References Cited

U.S. PATENT DOCUMENTS 2,371,519 A * 3/1945 Haynes ............................ 606/54
4,386,603 A * 6/1983 Mayfield ........................ 606/105
(Continued)

FOREIGN PATENT DOCUMENTS

| EP | 0 978 258 B1 | 10/2002 |
| WO | WO 90/02527 A1 | 3/1990 |
| WO | WO 2006/130085 A1 | 12/2006 |

OTHER PUBLICATIONS

International Search Report, PCT Application No. PCT/SE2009/000275, date of mailing Sep. 11, 2009 (5 pgs.).

(Continued)

*Primary Examiner* — Pedro Philogene
*Assistant Examiner* — David Comstock
(74) *Attorney, Agent, or Firm* — Cooley LLP; Brian P. Hopkins (57) ABSTRACT

Embodiments of the present disclosure are directed to a systems, devices and methods for displacing bones of a living mammal. In some embodiments, a device is provided which includes at least two engagement elements positioned at a distance from each other for engagement with two separate bones Each of the engagement elements may be carried by a support part which in turn is supported in a support portion of a distance unit (5). The said support part and support portion form a support unit, where each engagement element extends at an angle (α) with respect to a straight line (L) between two support units. At least one of the support units includes an arrangement for altering the angle which includes an actuating unit maneuverable for adjustment of the angle (α). Some embodiments of the disclosure are directed to a system for engagement with vertebrae including such devices (noted above), as well as uses of the device and associated methods of treatment.

12 Claims, 8 Drawing Sheets

(56) References Cited

U.S. PATENT DOCUMENTS

| | | |
|---|---|---|
| 4,611,580 A | 9/1986 | Wu |
| 4,658,809 A | 4/1987 | Ulrich et al. |
| 4,733,657 A | 3/1988 | Kluger |
| 4,854,304 A | 8/1989 | Zielke |
| 4,944,743 A | 7/1990 | Gotzen et al. |
| 5,219,349 A | 6/1993 | Krag et al. |
| 5,304,179 A * | 4/1994 | Wagner .................. 606/267 |
| 5,431,658 A * | 7/1995 | Moskovich .................. 606/99 |
| 6,565,568 B1 | 5/2003 | Rogozinski |
| 7,387,635 B2 * | 6/2008 | Keller .................. 606/99 |
| 2003/0055427 A1 | 3/2003 | Graf |
| 2004/0002758 A1 | 1/2004 | Landry et al. |
| 2004/0059271 A1 | 3/2004 | Berry |
| 2004/0148028 A1 | 7/2004 | Ferree et al. |
| 2004/0220567 A1 | 11/2004 | Eisermann et al. |
| 2004/0220582 A1 | 11/2004 | Keller |
| 2004/0225295 A1 | 11/2004 | Zubok et al. |
| 2005/0159651 A1 * | 7/2005 | Raymond et al. ........... 600/213 |
| 2005/0177156 A1 * | 8/2005 | Timm et al. .................. 606/61 |
| 2005/0203532 A1 | 9/2005 | Ferguson et al. |
| 2005/0245928 A1 | 11/2005 | Colleran et al. |
| 2008/0077155 A1 | 3/2008 | Diederich et al. |
| 2008/0172062 A1 * | 7/2008 | Donahue et al. .................. 606/104 |
| 2012/0136355 A1 * | 5/2012 | Wolfson .................. 606/59 |
| 2012/0184958 A1 * | 7/2012 | Knuchel et al. .................. 606/59 |

OTHER PUBLICATIONS

Written Opinion of the International Searching Authority, PCT Application No. PCT/SE2009/000275, date of mailing Sep. 11, 2009 (7 pgs.).

Written Opinion of the International Preliminary Examining Authority, PCT Application No. PCT/SE2009/000275, date of mailing May 4, 2010 (7 pgs.).

Supplementary European Search Report for Application No. EP 09 75 5134, date of completion of search report, Apr. 18, 2013.

Medtronic, "Cornerstone—SR Cervical Carbon Cage System", Announcement Medtronic., Jan. 1, 1998, pp. 1-11, XP007916830.

* cited by examiner

DISPLACEMENT DEVICE, USE AND SYSTEM THEREFORE

CROSS REFERENCE TO RELATED APPLICATIONS

This application is a national stage entry of PCT/SE2009/000275, having an international filing date of May 28, 2009, which claims priority to Swedish patent application no. SE 0801246-0, filed on May 28, 2008 and claims priority to U.S. Provisional Application No. 61/130,490, filed on May 30, 2008. Each of the foregoing disclosures are expressly incorporated herein in their entirety.

FIELD OF THE INVENTION

The invention concerns a device according to the preamble of claim 1 and a system for engagement with vertebrae in a spinal column including such a device. The invention also concerns a use of the device.

BACKGROUND OF THE INVENTION

WO 06130085 describes in general a positioning device and in particular a device, which is mainly used when positioning of a disc implant in combination with separating of vertebrae. The positioning of the disc implant results in accurate replacement of the disc that causes pain, reinstating the distance between the vertebrae and reinstating movability between them.

In particular, WO 06130085 discloses distance means that carry engagement means for the engagement with two vertebrae at a distance from each other. Said distance means are arranged such that they are capable of changing the degree of separation of said vertebrae when the engagement means are in engagement therewith. The possibility of spanning apart the vertebrae makes it possible, i.a. to freely remove the old disc.

When two distance means, carrying the engagement means, are arranged in parallel, handling of a holder and a prosthesis/an implant carried thereby takes place between these distance means.

In WO 06130085, the engagement means are connected to the distance means in friction joints such that the engagement means are movably fastened to the distance devices in order to avoid excess breaking forces in connection with separating vertebrae.

WO 9002527 concerns a distractor having parallel coupled first and second adjustment means for maneuvering engagement screws. This distractor gives limited possibilities for controlling the displacement of bones and is impractical for use in a real life situation.

AIM AND MOST IMPORTANT FEATURES OF THE INVENTION

Even if the background art device functions well, it is an aim of the present invention to obtain a more versatile solution which can be used more freely for various bone displacing functions.

This aim is achieved in a positioning device according to the above through the features of the characterizing portion of claim 1.

When the arrangement for altering the angle includes an actuating unit which is maneuverable for pivotal adjustment of said angle, it is made possible on the one hand to control the device so as to increase the possibilities to manipulate the bones. It is further made possible to simply provide firm support in chosen angles for the engagement elements in respect of the distance units.

This is advantageous compared to the device according to WO 06130085 which in practice does not make it possible to alter the angle between the engagement elements and the distance unit, unless the device is not subject to a load. Further, the friction lock joints provided according to WO 06130085 requires relatively hard tightening since forces affecting the engagement elements that can occur, in particular with respect of a spinal column, might be of unexpected high magnitude.

In the device of WO 9002527 it is practically impossible to achieve a controlled movement of the screws, because of the parallel coupled first and second adjustment means for maneuvering the engagement screws. Actuating of one of the first and second adjustment means of WO 9002527 will lead to altered angles of the screws such that the screws will become more separated distally than proximally and vice versa, which is not a desired effect. Pure parallel displacement of the screws is therefore not practically possible.

As a contrast, the device according to the invention has an arrangement allowing the angle of the respective engagement means to be independently adjustable, and parallel displacement is easily achieved.

The present invention makes it possible to choose, obtain and lock not only the separation but also the angular positions of the bones (in particular vertebrae) with respect to each other and individually with respect of the distance unit. It is thus also possible to straighten up vertebrae in respect of each other or to obtain other desired relative positioning thereof.

It is possible to "train" or mobilize ligaments also at inaccessible areas of a spinal column in a careful way, so as to create sufficient space between all parts of vertebrae for an implant leaving blood vessels, intestines, muscles etc. unharmed.

The engagement elements are preferably elongated and have substantially longitudinal axes. In particular the engagement elements have screw treads for uncomplicated engagement with bones.

When each support part is arranged to carry an engagement element in one mode where it is movable and in another mode where it is fixed, it is achieved that it can be engaged with a bone when in position in the device and subsequently be locked at a desired position.

It is preferred that one of the support part and the support portion includes a pivotal pin which is pivotally supported by a corresponding bearing in turn being included in the other one of the support part and the support portion because of simplicity reasons. In particular, the engagement element is pivotal in a plane substantially parallel to or even including a straight line between two support portions on one distance unit.

It is preferred that the actuating unit includes a setting element on one of the support parts and the support portion that is acting against a surface portion on the other one of the support part and the support portion. This provides a simple and simply operated solution. It is also preferred that the setting element is one from the group: a treaded sleeve, a screw, a nut, a cam.

The distance unit has preferably means for controlled displacement of the support units in respect of each other in order to alter the degree of separation of said bones, since this provision allows for greater separating possibilities. The means for controlled displacement is thereby advantageously one from the group: screw means, rack and pawl, lever mechanism, telescopic elements, pneumatic means, hydraulic means.

It is further preferred that it includes a special tool for manipulating said actuating unit and a tool for manipulating said engagement elements.

The invention also concerns a system for engagement with vertebrae in a spinal column including at least one device for separating bones and a holder for a prosthesis from the group: a disc implant, a vertebral implant, said holder being adjustably fixable to e.g. an engagement element in the form of a bone screw over a specially constructed positioning arrangement, said holder preferably including a fork-shaped head for external or internal cooperation with the implant.

The system preferably includes at least one supporting device which is fixed on said at lest one device for holding an operation point for engagement with vertebrae free from body organs.

The system according to the invention includes, in a preferred embodiment, a positioning arrangement for an implant, wherein a positioning arm has a first portion for engagement with said distance unit and a second portion for engagement with an implant holder, and wherein the holder can be locked in a desired position. This allows secure positioning of the implant when completing the process of replacing a damaged body part.

BRIEF DESCRIPTION OF DRAWINGS

The invention will now be described by way of embodiments and with reference to the annexed drawings, wherein:

FIG. 6 shows a part of an alternative engagement element according to the invention.

DESCRIPTION OF EMBODIMENTS

Figure 1:
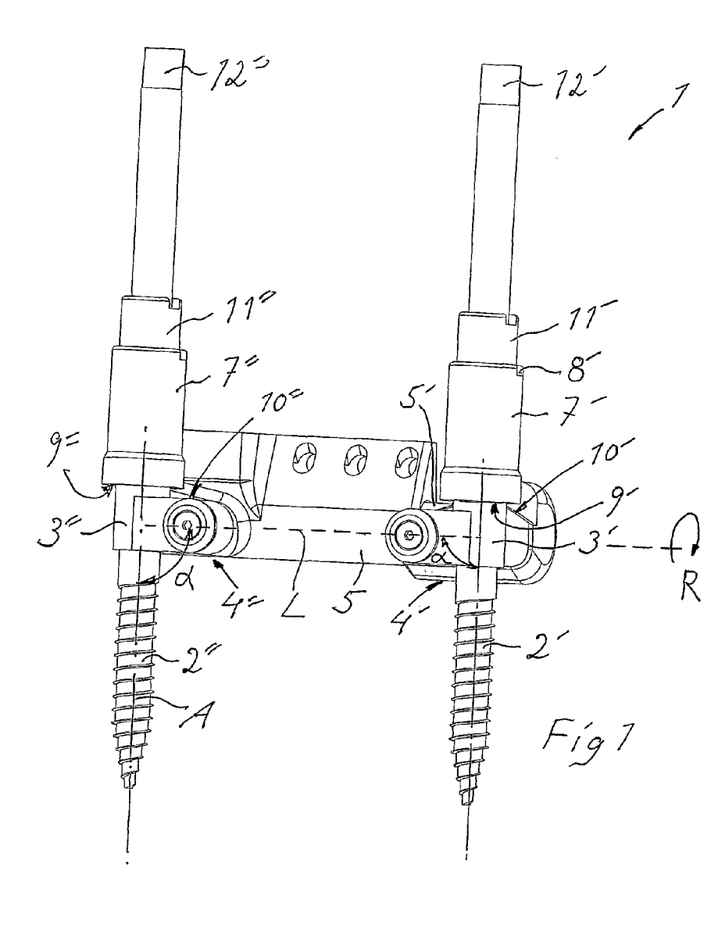
FIG. 1 shows a device according to the invention in a side view.

In FIG. 1, reference numeral 1 denotes a device for displacing bones. In particular the device 1 is intended and designed for the distraction of vertebra in a spinal column, so as to allow a surgeon access to an operation point between two vertebrae. The vertebrae are separated so as to e.g. remove a damaged disc in the process of replacing that disc with a prosthesis in the form a disc implant. In that process it is important to be able to completely clear out the region between the vertebrae, such that no parts of the damaged disc remain.

The device according to the invention simplifies the entire operation process which will result in a more secure and fast process.

The device 1 is comprised of two engagement elements 2' and 2" which are positioned at a distance from each other and are carried by respective support parts 3' and 3" which in turn are supported in support portions 4' and 4" of a distance unit 5. The distance unit 5 is telescopic and capable of being extended such that the support portions 4' and 4" and thereby the support parts 3' and 3" and thus the engagement elements 2' and 2" are displaced in respect of each other.

A (not shown) tube transmits hydraulic medium used for actuating the telescopic distance unit 5, said unit including a (not shown) piston-cylinder aggregate of a per se known kind.

The engagement elements 2' and 2" each have a longitudinal axis, whereof one, A, for the engagement element 2", is shown in the Figure. A straight line between the two support units which are each made up by a support part and an associated support portion is indicated with L. As shown in FIG. 1, the longitudinal axis A of engagement element 2" forms an angle α with said straight line L. In the shown embodiment, the line L is a symmetrical axis of a of the telescopic distance unit 5. Alternatively, it can be said that the angle α is between the longitudinal axis A of the respective engagement element 2' and 2" and a plane through L and the axis of the respective pivot pin 13' and 13" (see FIG. 3).

In the figure, 5' indicates a piston rod being part of said piston-cylinder aggregate of the telescopic distance unit 5. Extension of the telescopic distance unit 5 is thus accomplished by the piston rod 5' being forced out from the housing of the telescopic distance unit 5 in a manner which is per se known in respect of fluid operated piston-cylinder devices. Further, the piston rod 5' is rotatable (R in FIG. 1) in respect of the rest of the telescopic distance unit 5 such that the relative rotational position of the support portions 4' and 4" and thereby the engagement elements 2' and 2" in respect of the symmetrical axis of the telescopic distance unit 5 can be varied at will in order to adjust to various requirements on the particular case.

The engagement elements 2' and 2" are shown having tapering portions directed downwardly in FIG. 1, and these tapering portions are provided with threads which are intended to engage possibly pre-drilled holes in bones such as vertebrae to be manipulated.

On the upper ends of the engagement elements 2' and 2" there are positioned means for the control of the engagement elements in a way which will be explained below.

On the upper part of the engagement element 2' which is thus opposite to the tapering, threaded portion in respect of the support part 3', there is arranged a first rotatable sleeve 7' which is part of an actuating unit and is used for pivoted adjustment of the angle α. At that part of the engagement element 2' there is also arranged a second sleeve 11', which is used for locking the engagement element 2' inside the support part 3'.

The actuating unit in respect of the engagement element 2' functions such that the first sleeve 7', which has a threaded inside engagement with a treaded outside on the support part 3' (see FIGS. 5 and 6), through rotation of the first sleeve 7' will obtain an axial displacement along the support part 3' and thereby along the engagement element 2'. An end surface of the first sleeve 7' being directed axially and downwardly in FIG. 1 and being indicated with 9' co-operates with a cam surface 10' which is situated on the support portion 4'.

Through this arrangement, rotation of the first sleeve 7' for a movement in the direction towards the tapering portion of the engagement element 2', will result in that the angle α increases. On the other hand, when the first sleeve 7' is rotated such that it with its end surface 9' is displaced in a direction away from the tapering portion of the engagement element 2', the angle α will decrease.

Figure 5A:
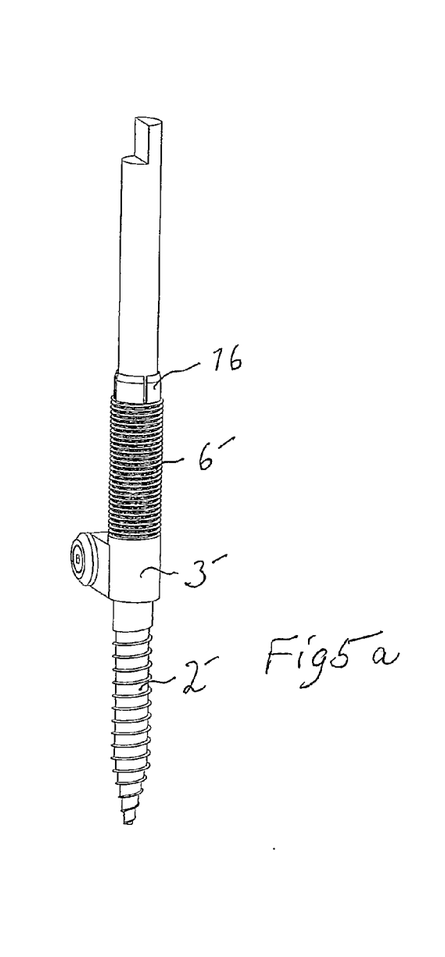
Figures 5B, 6:
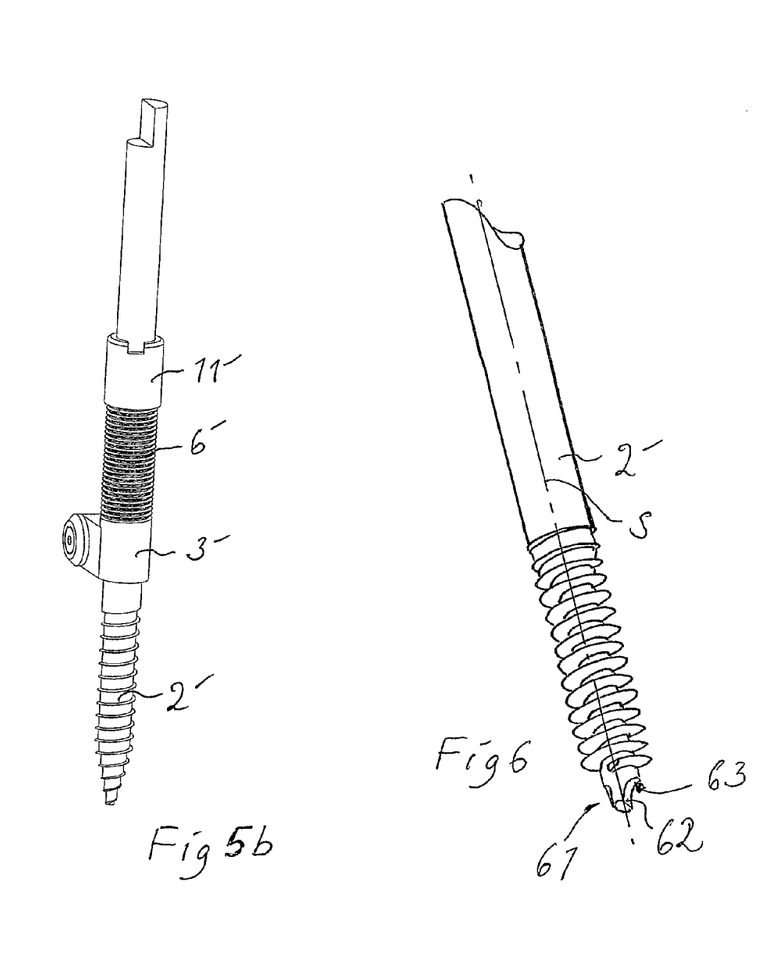

Rotation of the second sleeve 11' is between a first mode, where the engagement element 2' is free to move axially inside the support part 3' as well as to rotate inside the support part 3', and a second mode, where the engagement element 2' is locked from axial movement and from rotation. Such a locking function can be easily accomplished for example by having an inside portion of the second sleeve 11' being inwardly conical and co-operating with a small sleeve surrounding the engagement element 2' and having a correspondingly conical upper outside surface (see FIG. 5).

12' and 12" indicate wrench engagement surfaces in the form of cut-ins so as to form planar surface portions. The engagement elements can of course also have other means for engagement with a wrench such as e.g. Allen key holes.

The upper part of the first sleeve 7' is shown having a notch 8', which is intended to be engaged with a corresponding protrusion of a tool used for manipulating the device 1 as will be described below. A corresponding notch is present on the second sleeve 11.

Figure 2:
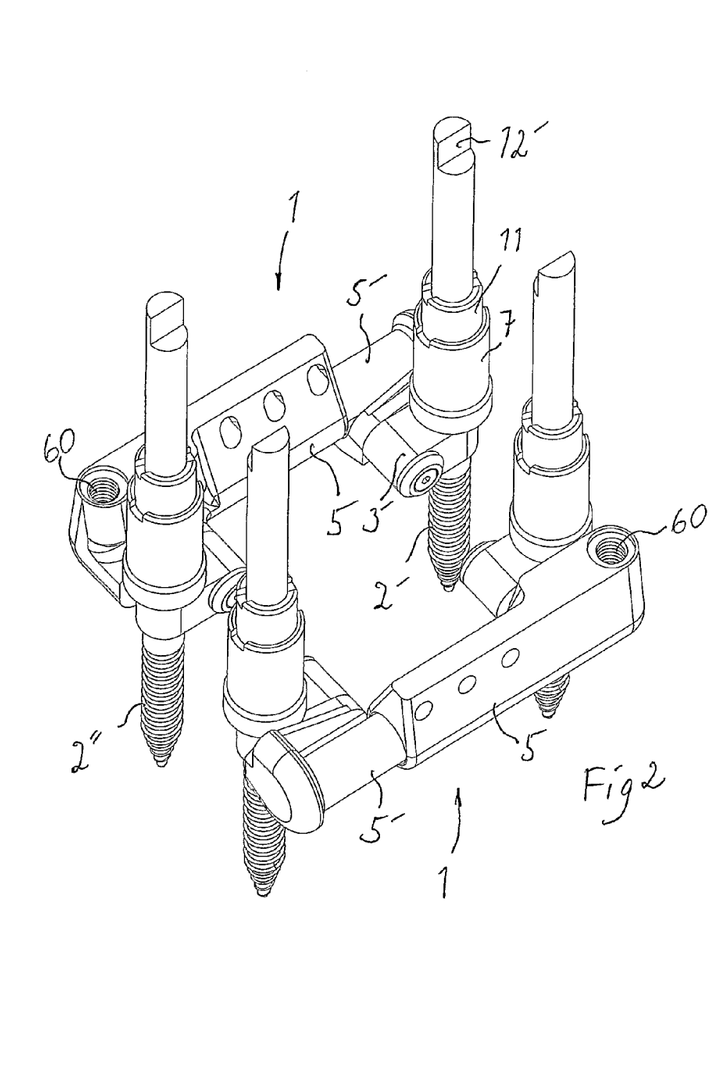
FIG. 2 shows two devices according to the invention in a perspective view.
Figure 7:
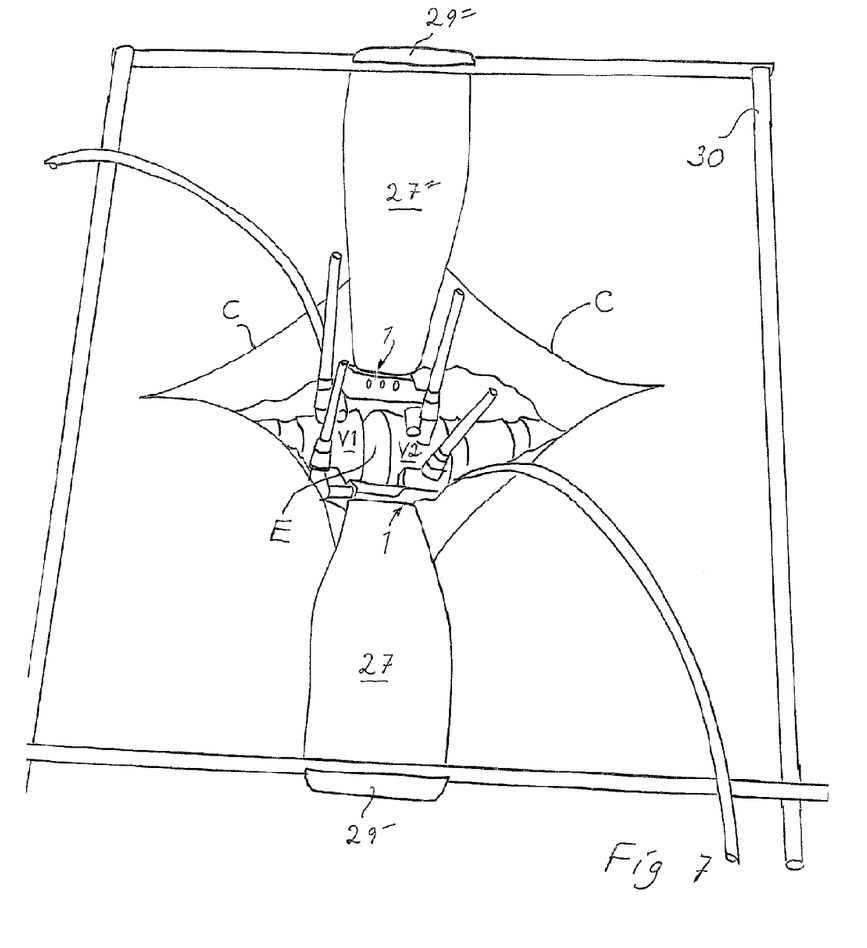
FIG. 7 shows parts of a system according to the invention during use.
Figure 10A:
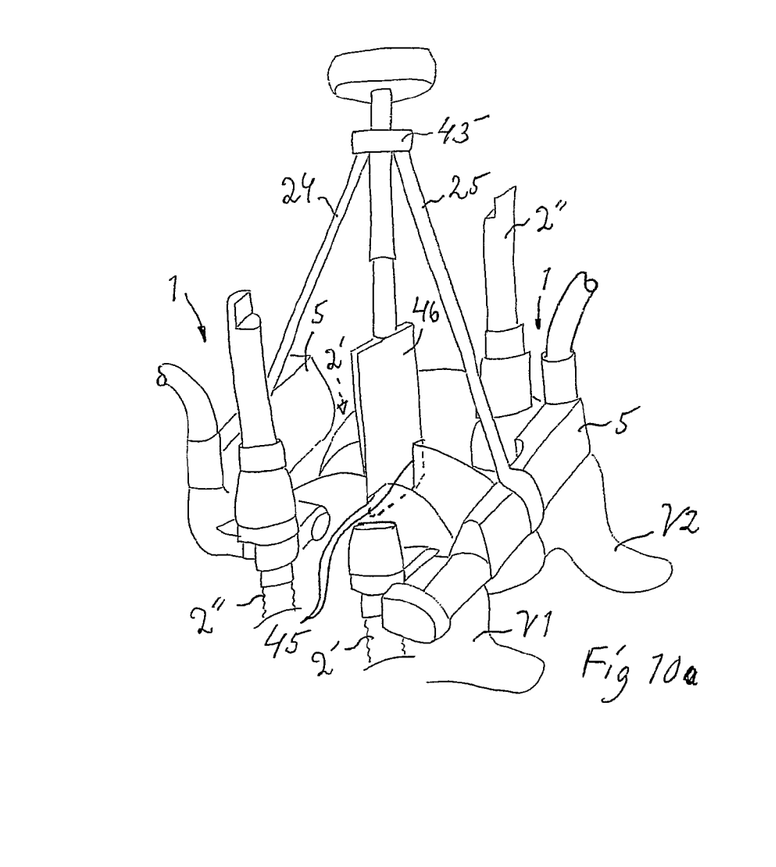

The device according to the invention is most often used in pairs, which is shown in FIG. 2. The two devices in FIG. 2 are identical for better ease of handling. Normally, when the device is installed in respect of bones such as vertebrae to be displaced (see also FIGS. 7 and 10*a-c*), firstly the engagement elements 2' and 2" are screwed into two adjacent vertebrae, whereby as advantageous positions as possible can be chosen in respect of bone strength etc. Thereupon the telescopic distance units 5 are positioned by the support parts 3' and 3" being slid over and onto the fastened engagement elements 2' and 2" such that their relative position will correspond essentially to what is shown in FIGS. 2, 7 and 10*a* and *c*. By the support portions 4' and 4" being rotational with respect to each other and by the support parts 3' and 3" being pivotal, it should be understood that there is easy to find positions of the support parts 3' and 3" of the device 1 such that bores inside the sleeves 7', 7" can receive the engagement elements 2' and 2". Thereafter, the sleeves can be tightened for locking the engagement elements 2' and 2" and finally the displacement device be actuated for displacement.

60 indicates holes for the connection of hoses for hydraulic fluid. When fluid is introduced into the distance units 5, the piston rod 5' is pressed out from the telescopic distance unit 5 so as to obtain a separating action.

Figure 3:
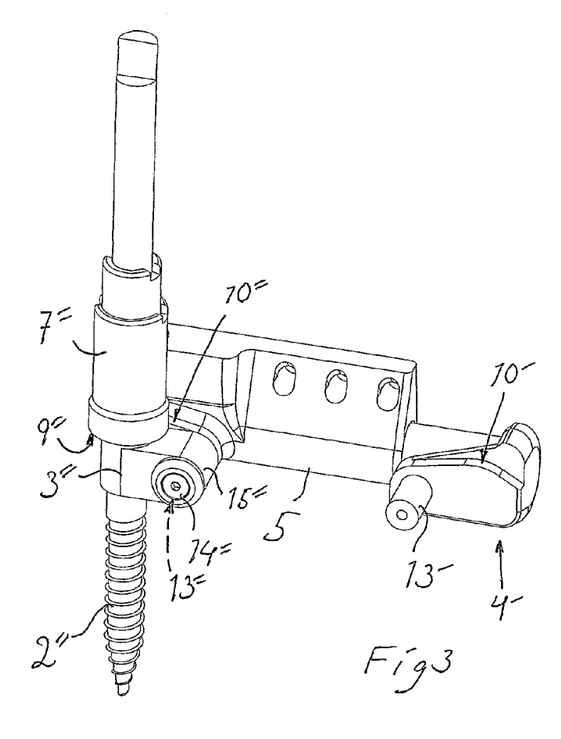
FIGS. 3 and 4 show the device in FIG. 1 in perspective views with parts removed for clarity, FIGS. 5a and b show parts of a device according to the invention.
Figure 4:
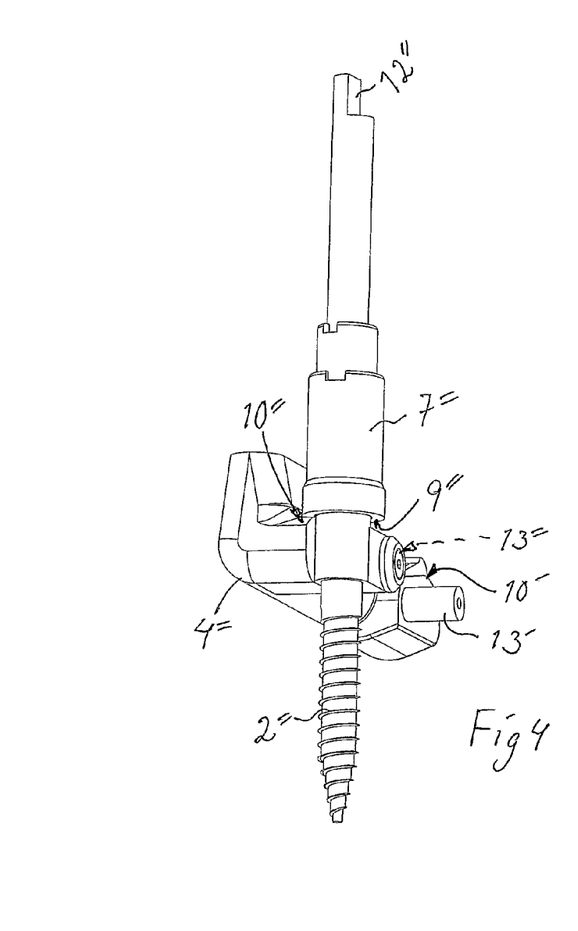

In FIGS. 3 and 4 are shown more details in respect of the support unit, wherein i.a. is shown in more detail a pivot pin 13', which is part of the support portion 4', stripped from the support part 3'. 14" indicates a washer/screw combination for securing the support part 3" on a pivot pin (not shown) corresponding to the pivot pin 13' and carrying a bearing portion 15" of the support part 3". In these figures, the co-operation between the end surface 9" and the cam surface 10" is shown in more detail.

With reference to all of FIGS. 1, 3 and 4, since the support part 3' provides a distance between the pivot axis, being the axis of the pin 13', and the point of engagement between the surface 9' of the first sleeve 7' and the cam surface 10' of the support portion 4', the degree of adjustment of the angle α will be dependent on the distance between these points.

FIG. 5*a* shows the support part 3' and the engagement element 2' in more detail. In FIG. 5*a*, the first and second sleeves (see FIG. 1) are removed and a treaded portion 6' is shown in its entirety. The treaded portion 6' co-operates with both of the first and second sleeves which thus have correspondingly threads inside. The locking function for locking the engagement element 2' mentioned above is accomplished by having a inside portion of the second sleeve 11' being inwardly conical and co-operating with a small, interrupted sleeve 16 on the engagement element 2' and having a correspondingly conical upper outside surface. Tightening of the sleeve 11' (see FIG. 5*b*) will accomplish clamping of the interrupted sleeve 16 on the engagement element 2' and locking it to the support part 3'.

Such arrangements are per se known in various arrangements, for example in respect of pipe couplings, and are therefore not further explained here.

FIG. 6 shows an alternative the engagement element 2' in more detail. This engagement element 2' is distinguished from the one shown in previous figures in that the screw point 61 is constructed differently, with a peg-shaped extension 62 and an abutment surface 63, which forms a blunt angle to a symmetry axis S through the element 2'. This construction makes it easier to detect when the screw (element) 2' has reached a correct position in a vertebra, since it makes it possible for the surgeon to sense when the screw has passed the front cortical part thereof, the spongy inside of the vertebra and reached the rearward cortical part thereof such that the screw will be accurately engaging the hard portions of the vertebra in front and rear portions for best reception of the load.

FIG. 7 shows, diagrammatically, a system including two devices 1 for displacing two adjacent vertebrae V1 and V2 in a spinal column which is accessed through a cut C through the abdomen of a patient. The system is shown in an early step in the process of replacing a damaged disc in a spinal column of a human with an implant. The system includes an arrangement according to the invention, wherein the devices 1 have been activated so as to separate the vertebrae V1 and V2.

The damaged disc has been removed so as to leave an empty space E between the vertebrae V1 and V2, wherein an implant is intended to be positioned. The two devices 1 are here shown completed with deflectors 27' and 27" that are designed to deflect sides of the cut C and body organs in the region of the operation point so as to allow better working conditions for the surgeon. Hereby, firstly, the spinal column is somewhat lifted in respect of the abdomen, giving the surgeon better working space and reduced depth through the cut C down to the spinal column. Secondly, the body organs are gently removed from the operation point and securely stabilized sideways thereof.

Figure 9A:
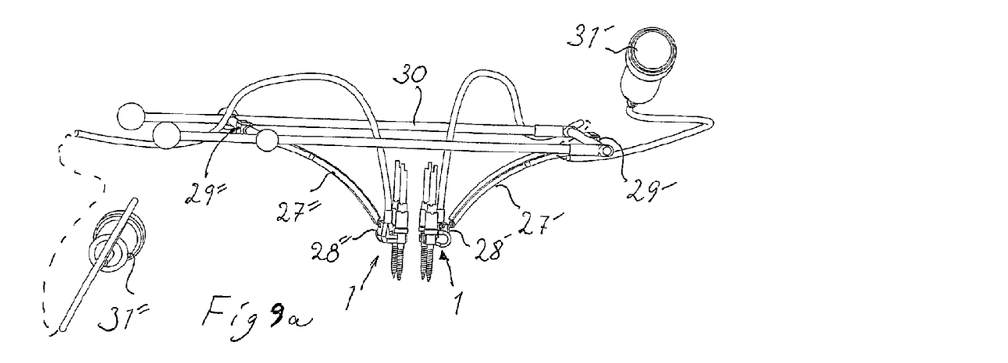

The deflectors 27' and 27" include slightly curved panel portions and hook-like, first fastening portions, which are best shown in FIG. 9*a* and indicated with 28' and 28", for engagement with the respective distance unit 5. Further, the deflectors include, hook-like, second fastening portions 29' and 29" for the engagement with a tightening frame 30, having transversal elements for engagement with the second fastening portions 29' and 29" and longitudinal elements forming a rectangular frame 30. The transversal elements can be separated so as to obtain a down-holding and spreading effect to the deflectors 27' and 27".

Figure 8:
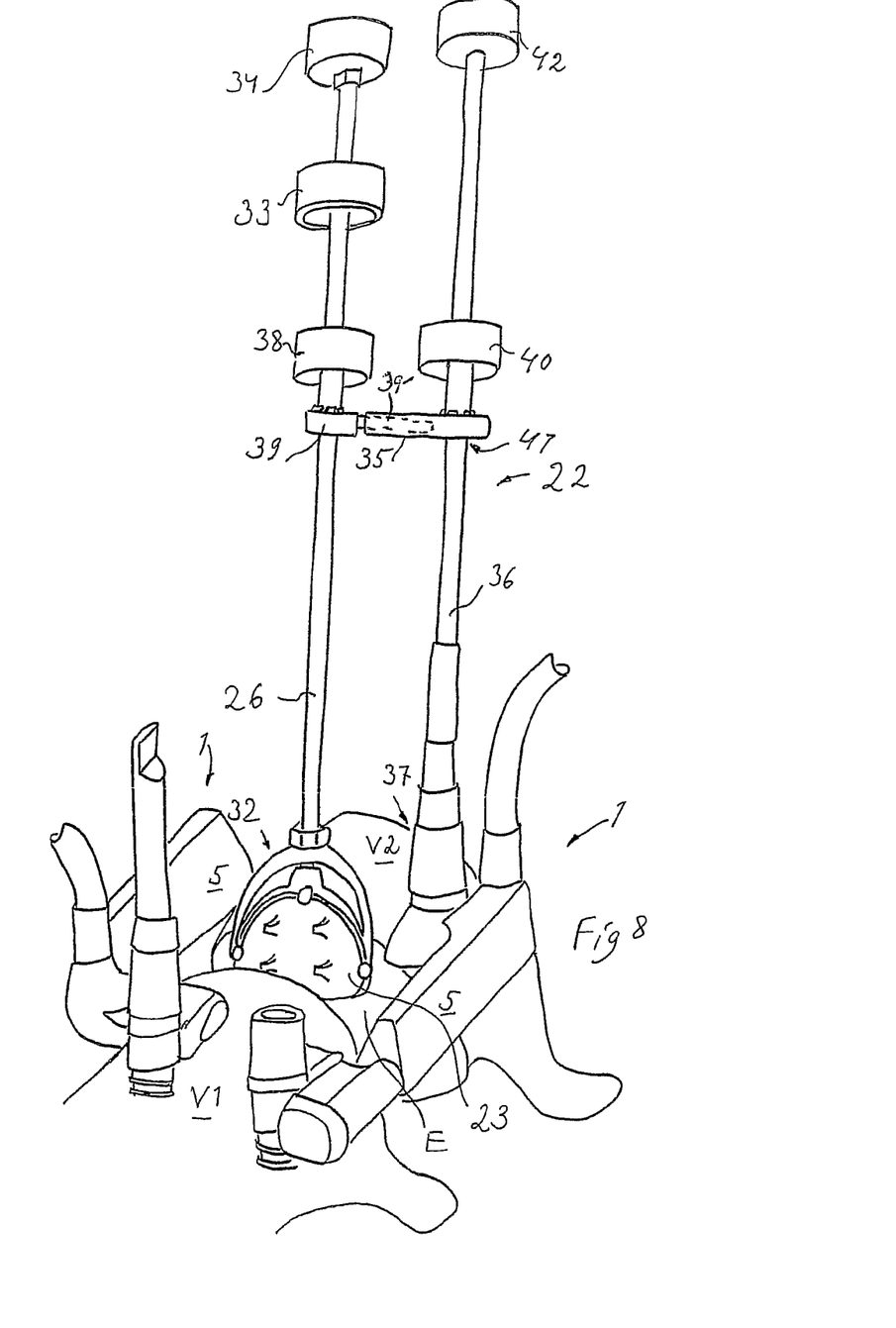
FIG. 8 shows the system with an implant holder, FIGS. 9 a and b show a system according to the invention in different views, FIGS. 10 a-b show parts of a system according to the invention during a second form of use, a tool for the manipulation of the device.

FIG. 8 shows diagrammatically a later step in the process of replacing a damaged disc. Here the deflectors and also other details are removed for clarity purposes only. The system is here shown with a positioning arrangement 22 for an implant 23. An exemplary embodiment of a holder 26 for the implant 23 has a gripper head 32 which can be manipulated by relative axial movements of two knobs 33 and 34.

The holder 26 is over a an extendable and mutually lockable support member 35, 39 connected to a positioning arm in the form of a fixing device 36 which can be fastened (at 37) to the upper part of one of the engagement elements of the device in the above mentioned figures. A rotation and slide joint, at 41, can be locked so as to lock a stem portion of the fixing device 36 to the support member 35, 39 for preventing any mutual movement (slide through and articulation of the joint) of these elements by rotating a locking knob 40.

By rotating a second locking knob 38 maneuvering a similar rotation and slide joint at 39, the holder 26 can be locked to the support member at the end with numeral 39 in the same way. At the same time, a slotted portion 39', which is fitted inside a channel, (not shown) in the element indicated with 35 is brought to expand sideways, whereby a mutual telescopic movement of the element 39,39' in respect of the element 35 can be locked.

Locking of 38-39, 35-39 and 40-41 thus results in complete locking of the entire positioning arrangement 22.

In practice, the joints at 39 and 41 are per se known joints with slotted spherical sleeves, each including a conical, inner, axially displaceable elements allowing free manipulation in released state and providing locking in the locked state. By rotating the locking knob, the conical, inner, axially displaceable element provokes an expansion of the slotted spherical sleeve and locks the angle and the passage through the joint.

In locked mode, thus the guiding head 32 fixes the position of the implant 23 prior to releasing the device 1 for displacing/separating the vertebrae so that it can be ensured that the implant is correctly positioned, for example with the aid of real time X-ray imaging.

Further, when releasing the devices 1, the vertebrae are allowed to approach each other with the implant accurately positioned in between.

For the sake of clarity, parts of engagement elements have been removed. In this case, as is normally the case, two engagement elements have been screwed into each one of the vertebrae, whereupon the telescopic distance units 5 (see e.g. FIG. 1) have been actuated for separation of the vertebrae V1 and V2. The angular adjustment of the engagement elements can then be individually set by rotation of the respective first sleeves 7' and 7" (see e.g. FIG. 1). Hereby the angles between the vertebrae can be accurately adjusted if necessary.

In order to arrange a greater space between two distance devices, the attachments of the engagement means are most preferred positioned sideways, outwardly, so that the distance units can be positioned sideways with respect of the axes of the engagement means.

Figure 9B:
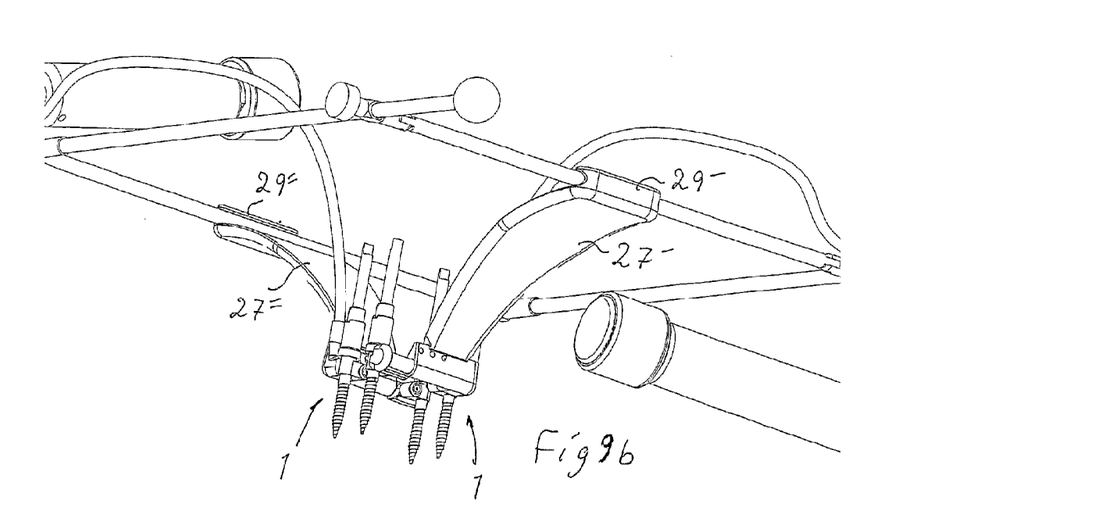

FIGS. 9a and b show an arrangement according to the invention, with the devices 1 completed with the deflectors 27' and 27".

31' and 31" indicate hydraulic pressurizers for supplying hydraulic fluid to the distance units upon rotation of respective end knobs.

Tools for rotating the first and second sleeves 7' and 7" (see FIG. 1) can be designed to have tubular parts that are provided with protrusions on one end for co-operation with the notches of the sleeves. On an opposite end, the tubular parts can have rotation knobs. In order to rotate the sleeves, the tubular parts are simply slid over the free portions of the engagement elements.

Figure 10B:
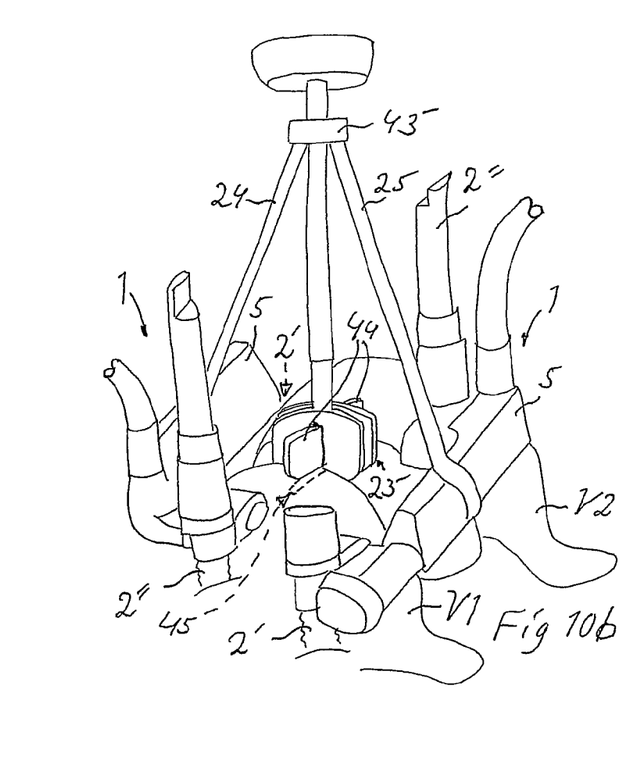

FIGS. 10a and b shows the inventive system including two devices 1 for displacing two adjacent vertebrae V1 and V2 in a spinal column in the process of positioning an alternatively configured implant 23' which is provided with a guiding fin 44 extending outwardly on each side of the implant 23'. In order to make guiding slots 45 in the vertebrae, the system is used according to what is shown in FIG. 10a, wherein is shown a slot knife 46 being supported by the slide guide 43'.

The slot knife 46 is thus pressed-in between the vertebrae when these are separated a predetermined distance, such that slots 45 having an adequate depth and width are formed in the adjacent vertebrae.

This use of the inventive system provides an advantage compared to the background art, since it gives the possibility to form the slots 45 in the vertebrae in a simple way with precision and little effort. The implant 23' can subsequently be positioned as is shown in FIG. 10c with the fins 44 being guided by the slots 45 into a desired position between the vertebrae V1 and V2.

In common for the positioning in FIGS. 8 and 10b is that the implant can be positioned gently without requirement for the relatively violent hammering action, which unfortunately has to be employed for implanting discs according to today's common practice.

Figure 11:
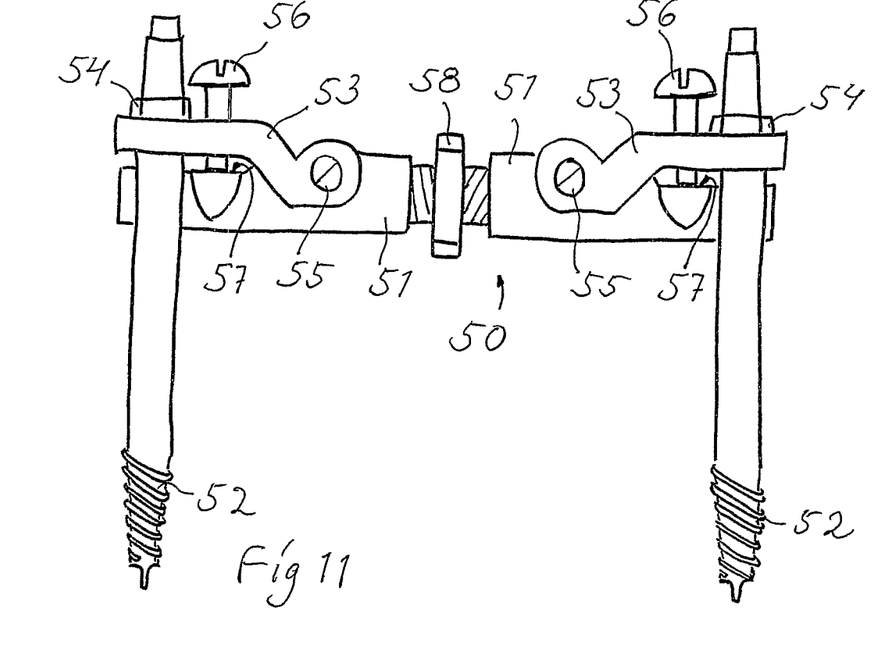
FIG. 11 shows an alternative displacement device.

FIG. 11 shows a variant of a device 50 according to the invention, wherein two end parts 51 are mutually rotational and displaceable by the intermediate of a centre screw-treaded element 58 such that these parts together form a rigging screw-like construction, whereby rotation of the element 58 displaces the end parts 51. Engagement elements 52 are locked with sleeves/nuts 54 and carried by support parts 53 that are pivotal over pins 55. The angular relationship between the engagement elements 52 and the parts 51 are adjusted by set screws 56 engaging counterparts 57 on the end parts.

Various modifications of the invention can be made within the scope of the claims. The system can have one single displacement device instead of two. At the ends, this single unit can have sideward angled bracket portions for co-operation at different positions along their lengths with typically each two engagement means that are engaged with the vertebrae so that the device according to the system will have a shallow U-shaped construction with the distance unit as the web and the sideward angled portions as the shanks of the U. In this case positioning, as an example, may need to be arranged on the one hand on the only distance device, on the other hand on a fixed point on a vertebra.

Also other kinds of arrangements for locking the holder can be envisaged, for example with a locking device arranged at the fastening point of the arms 24 and 25. It is also possible to have other types of locking devices and it is possible to use a plurality of separate locks instead of an integrated lock. The distance units can be manipulated otherwise, for example by screwing, with a notched rod with possibly spring loaded locking device, or with a lever mechanism.

In a simple modification, the distance unit is maneuvered with the aid of an adjustment cable, such as a "Bowden cable", which can have its fastenings on engagement portions on mutually movable parts of a distance device in a manner which is per se obvious for the person skilled in the art. Other means for angular adjustment can also be employed.

It shall be noted that it is not excluded that other prostheses are positioned with a device according to the invention, for example vertebrae prostheses.

The invention claimed is:

1. A bone displacement device for displacing bones relative to one another in a living mammal, the device comprising:
    first and second support units each comprising a support portion and a support part, the support part having external threads and being supported by the support portion, wherein the first support part of the first support unit includes a pin in pivotal cooperation with a bearing provided in the second support part, a distance unit having controlled displacement means for controlling displacement between the support units with respect to one another to alter the degree of separation of the bones;

at least two elongated engagement elements spaced apart from one another for engagement with at least two separate bones, the engagement elements comprising at least a first engagement element and a second engagement element each having a substantially longitudinal axis, wherein     each engagement element is housed by a respective support part, and     each engagement element extends at a respective angle with respect to a straight line between the support units, and angle-altering means provided with at least one of the support units configured to accurately alter the angle between the engagement elements and thus, the associated bones, the angle-altering means comprising an actuating unit maneuverable to adjust the angle via the respective support part, wherein the actuating unit includes     a setting element comprising a cam arranged on the first support part and configured to act against a surface portion on the second support part, and     a sleeve having an end surface and internal threads for engagement with the external threads of the support part, wherein         the sleeve is configured to axially displace upon rotation along the support part and thereby correspondingly along the engagement element,         the end surface of the sleeve is directed axially and cooperates with the cam, and         the angle-altering means operates in at least two modes: an adjustment mode where the angle between engagement elements can be altered, and a locked mode where the angle between engagement elements is locked in position, the locked mode occurring upon interaction of the end surface of the sleeve with the cam of the at least one support unit.

2. The device according to claim 1, wherein the engagement elements have screw treads for engagement with bones.

3. The device according to claim 1, wherein the distance unit is telescopic and capable of being extended such that the support portions and thereby the support parts and thus the engagement elements are displaced in respect of each other.

4. The device according to claim 1, wherein the support portions of one distance unit are rotational relative to each other around a symmetry axis for a piston-cylinder aggregate being included in the distance unit.

5. The device according to claim 1, wherein the distance unit further comprises a piston-cylinder aggregate having a symmetry axis, and wherein the support portions of the distance units are rotational relative to each other around the symmetry axis.

6. The device according to claim 1, wherein the device is configured to displace vertebrae in a spinal column.

7. A system for engagement with vertebrae in a spinal column comprising at least one device according to claim 1, and a holder for a prosthesis, the holder selected from the group consisting of: a disc implant, a vertebral implant, wherein the holder is configured to be adjustably fixable to the at least one device.

8. The system according to claim 7, wherein the holder includes a fork-shaped head for external or internal co-operation with the implant.

9. The system according to claim 1, further comprising at least one deflector which is fixed on the at least one device, the deflector configured for holding an operation point for engagement with vertebrae free from body organs.

10. The system according to claim 1, wherein the system further comprises positioning means for an implant having at least one positioning arm with a first portion for engagement with the displacement device and a second portion for engagement with a holder for an implant, and wherein the holder is fastenable in a desired position.

11. The system according to claim 1, wherein the system further comprises a tool for manipulating the actuating unit.

12. The system according to claim 1, wherein the system further comprises manipulation means for manipulating the engagement elements.

* * * * *